US008647609B2

(12) United States Patent
Kim et al.

(10) Patent No.: US 8,647,609 B2
(45) Date of Patent: Feb. 11, 2014

(54) COMPOSITE POWDER FOR SIMULTANEOUSLY BLOCKING INFRARED AND ULTRAVIOLET RAYS AND COSMETICS COMPOSITION USING THE SAME

(75) Inventors: Seong Rae Kim, Seoul (KR); Seung Ki Lee, Cheonan-si (KR); Deok Ki Seo, Cheonan-si (KR); Kun Kook Lee, Seoul (KR)

(73) Assignee: Coreana Cosmetics Co., Ltd., Cheonan-Si (KR)

( * ) Notice: Subject to any disclaimer, the term of this patent is extended or adjusted under 35 U.S.C. 154(b) by 63 days.

(21) Appl. No.: 13/257,873

(22) PCT Filed: Jun. 14, 2010

(86) PCT No.: PCT/KR2010/003813
§ 371 (c)(1),
(2), (4) Date: Sep. 20, 2011

(87) PCT Pub. No.: WO2011/010798
PCT Pub. Date: Jan. 27, 2011

(65) Prior Publication Data
US 2012/0015015 A1    Jan. 19, 2012

(30) Foreign Application Priority Data

Jul. 24, 2009   (KR) .................. 10-2009-0067886

(51) Int. Cl.
*A61K 8/27* (2006.01)
*A61K 8/29* (2006.01)
*A61K 9/14* (2006.01)
*A61K 33/30* (2006.01)
*A61Q 17/04* (2006.01)

(52) U.S. Cl.
USPC ............. 424/59; 424/401; 424/489; 424/490; 424/617; 424/642

(58) Field of Classification Search
None
See application file for complete search history.

(56) References Cited

U.S. PATENT DOCUMENTS 5,456,749 A * 10/1995 Iwasa et al. .................. 106/417
5,688,439 A * 11/1997 Chopin et al. ................. 516/33
(Continued)

FOREIGN PATENT DOCUMENTS

CN    1478455 A    3/2004
CN    1494413 A    5/2004
(Continued)

OTHER PUBLICATIONS

Mochizuki (Phys. Stat. Sol. 1981, (b) 107; pp. K53-K56).*
(Continued)

*Primary Examiner* — Ernst Arnold
(74) *Attorney, Agent, or Firm* — Sughrue Mion, PLLC

(57) ABSTRACT

Disclosed is composite powder comprising infrared-ray blocking particles; and ultraviolet-ray blocking particles coated onto one surface of each of the infrared-ray blocking particles, and cosmetics composition using the same, wherein the composite powder using both the infrared-ray blocking particle and the ultraviolet-ray blocking particle enables to simultaneously block the infrared and ultraviolet rays. Thus, if the composite powder of the present invention is applied to the cosmetics, it is possible to minimize the rough wrinkles, irregular pigmentary deposits, loss of skin elasticity, disturbance of skin barrier function, skin damages such as cancer of the skin, and skin aging, and also to boost SPF (Sun Protection Factor) and PA (Protection Factor of UVA) of the related art sunscreen. Especially, the present invention uses the composite powder prepared by coating one surface of the infrared-ray blocking particle with the ultraviolet-ray blocking particles, instead of mixing powder prepared by simply mixing the infrared-ray blocking particle and the ultraviolet-ray blocking particle. That is, since the small-sized ultraviolet-ray blocking particles are coated onto and stably fixed into the surface of the infrared-ray blocking particle, it is possible to prevent aggregation of the ultraviolet-ray blocking particles, thereby preventing deterioration in uniformity of adhesion to the skin, and deterioration of the ultraviolet-ray blocking efficiency.

12 Claims, 7 Drawing Sheets
(1 of 7 Drawing Sheet(s) Filed in Color)

(56) References Cited

U.S. PATENT DOCUMENTS

| | | | |
|---|---|---|---|
| 2007/0140984 A1* | 6/2007 | Kusano et al. | 424/49 |
| 2007/0253989 A1 | 11/2007 | Abe et al. | |
| 2008/0305133 A1 | 12/2008 | Berg-Schultz et al. | |
| 2010/0021509 A1 | 1/2010 | Matsumoto et al. | |
| 2010/0202991 A1 | 8/2010 | Simon et al. | |

FOREIGN PATENT DOCUMENTS

| | | |
|---|---|---|
| CN | 10365412 A | 2/2009 |
| JP | 61-293906 A | 12/1986 |
| JP | 09-099246 A | 4/1997 |
| JP | 09-132514 A | 5/1997 |
| JP | 09-143030 A | 6/1997 |
| JP | 11-180829 A | 7/1999 |
| JP | 2000-072622 A | 3/2000 |
| JP | 2002-234827 A | 8/2002 |
| JP | 2007-308395 A | 11/2007 |
| KR | 10-9744945 B1 | 8/2007 |
| WO | 02/22098 A2 | 3/2002 |
| WO | 2005-171145 A | 6/2005 |
| WO | 2008/044385 A1 | 4/2008 |

OTHER PUBLICATIONS

European Patent Office, European Search Report isssued in corresponding EP Application No. 10802391.2, dated Dec. 19, 2012.
Chinese Patent Office, Chinese Office Action issued in corresponding CN Application No. 201080014861.5, dated Aug. 29, 2012.
Japanese Patent Office, Japanese Office Action issued in corresponding JP Application No. 2011-551996, dated Aug. 6, 2013.

* cited by examiner

LEFT SIDE: CONTAINING MPT-136,
RIGHT SIDE: CONTAINING COMPOSITE POWDER

COMPOSITE POWDER FOR SIMULTANEOUSLY BLOCKING INFRARED AND ULTRAVIOLET RAYS AND COSMETICS COMPOSITION USING THE SAME

CROSS REFERENCE TO RELATED APPLICATIONS

This application is a National Stage of International Application No. PCT/KR2010/003813 filed Jun. 14, 2010, claiming priority based on Korean Patent Application No. 10-2009-0067886 filed Jul. 24, 2009, the contents of all of which are incorporated herein by reference in their entirety.

TECHNICAL FIELD

The present invention relates to functional powder for simultaneously blocking infrared and ultraviolet rays, and more particularly, to powder for preventing skin from aging and being damaged by solar rays.

BACKGROUND ART

Skin aging may be largely classified into two types: the first type is chronologic aging of the skin which is unavoidable with the lapse of time; and the second type is photoaging of the skin. The photoaging is observed when the skin on the face, the back of the hand, and the posterior neck are exposed to the solar rays for a long time. The photoaging is caused by the chronologic aging and ultraviolet rays.

The photoaging relates with rough wrinkles, irregular pigmentary deposits, loss of skin elasticity, disturbance of skin barrier function, and cancer of the skin. The photoagaing can be prevented by avoiding the exposure to the ultraviolet rays. Recently, it is disclosed that the infrared rays which occupy 54% of solar energy are among the environmental factors for accelerating the skin aging by a thermal effect.

As the environmental contamination results in the depletion of ozone layer, the skin may be easily aging and damaged due to the increased exposure to the ultraviolet rays. In order to prevent the skin from being damaged by the ultraviolet rays, cosmetics with sunscreen added therein have been developed.

The sunscreen may be largely classified into organic-based sunscreen and inorganic-based sunscreen.

The organic-based sunscreen comprises ingredients with conjugated bond capable of absorbing the ultraviolet rays in a molecular structure. This organic-based sunscreen might cause problems of skin toxicity, allergy to the skin, and discoloration.

The inorganic-based sunscreen comprises powder for scattering the ultraviolet rays, for example, metal oxide with a high refractive index. In case of the inorganic-based sunscreen, the above problems caused by the organic-based sunscreen would not occur. Recently, the inorganic-based sunscreen is widely used in view of safety. However, the powder such as the metal oxide constituting the inorganic-based sunscreen has strong aggregation so that a lump of powder is increased in size due to the powder aggregation. In this case, the lump of powder with the increased size may deteriorate the feeling to the skin and the adhesion to the skin, and may lower the efficiency of sunscreen.

Accordingly, if using the inorganic-based sunscreen, it is necessary to overcome the above problems caused by the powder aggregation. However, a method for preventing the above problem of the powder aggregation has not been proposed yet.

There are many reports informing that the ultraviolet rays of the solar rays especially have adverse effects on the human body. Thus, blocking the ultraviolet rays was a matter of primary concern in the cosmetics. However, the newest reports disclose that the infrared rays also have adverse effects on the human skin. Thus, it needs to provide a method for preventing the skin from being damaged by the infrared rays, but there is no proposed method.

Technical Problem

Therefore, the present invention is directed to composite powder and cosmetics composition using the same that substantially obviates one or more of the problems due to limitations and disadvantages of the related art.

An aspect of the present invention is to provide composite powder which facilitates to prevent particles for preventing skin damaging from being aggregated, and to minimize rough wrinkles, irregular pigmentary deposits, loss of skin elasticity, disturbance of skin barrier function, skin damages such as cancer of the skin, and skin aging by simultaneously blocking infrared and ultraviolet rays, and cosmetics composition using the above composite powder.

Technical Solution

To achieve these objects and other advantages and in accordance with the purpose of the invention, as embodied and broadly described herein, there is provided a composite powder comprising: infrared-ray blocking particles; and ultraviolet-ray blocking particles coated onto one surface of each of the infrared-ray blocking particles.

At this time, the ultraviolet-ray blocking particles are coated onto the entire surface of the infrared-ray blocking particle.

Also, the ultraviolet-ray blocking particles are coated onto the surface of the infrared-ray blocking particle while penetrating into the inside of the infrared-ray blocking particle.

At least one of the infrared-ray blocking particle and ultraviolet-ray blocking particle is surface-treated with an organic or inorganic surface treating agent containing a hydroxyl group (—OH) or hydrogen group (—H).

Furthermore, a weight ratio of the ultraviolet-ray blocking particle to the infrared-ray blocking particle is 1:99~99:1.

Also, a diameter of the infrared-ray blocking particle is within the range of 0.38~1.5 μm; and a diameter of the ultraviolet-ray blocking particle is within the range of 8~150 nm.

The infrared-ray blocking particle is formed of titanium dioxide ($TiO_2$) or zinc oxide (ZnO), and the ultraviolet-ray blocking particle is formed of a material or a mixture of two materials selected from a group including titanium dioxide ($TiO_2$), zinc oxide (ZnO), cerium dioxide ($CeO_2$), and zirconium dioxide ($ZrO_2$).

The infrared-ray blocking particle blocks infrared rays having the wavelength range of 760 nm ~3000 nm; and the ultraviolet-ray blocking particle blocks ultraviolet rays having the wavelength range of 290 nm ~400 nm.

In another aspect of the present invention, there is a cosmetics composition comprising the composite powder of the above structure as an effective component.

The infrared-ray blocking particle of the composite powder is about 1%~25% by weight of the cosmetics composition.

The cosmetics composition is prepared in type of a solution of water-in-oil emulsion or oil-in-water emulsion, suspension, emulsion, paste, gel, cream, lotion, powder, soap, surfactant-containing cleaning oil, powder-type foundation, emulsion-type foundation, wax-type foundation, or spray type.

Advantageous Effects

According to the present invention, the composite powder using both the infrared-ray blocking particle and the ultraviolet-ray blocking particle enables to simultaneously block the infrared and ultraviolet rays. Thus, if the composite powder of the present invention is applied to the cosmetics, it is possible to minimize the rough wrinkles, irregular pigmentary deposits, loss of skin elasticity, disturbance of skin barrier function, skin damages such as cancer of the skin, and skin aging, and also to boost SPF (Sun Protection Factor) and PA (Protection Factor of UVA) of the related art sunscreen.

Especially, the present invention uses the composite powder prepared by coating one surface of the infrared-ray blocking particle with the ultraviolet-ray blocking particles, instead of mixing powder prepared by simply mixing the infrared-ray blocking particle and the ultraviolet-ray blocking particle. That is, since the small-sized ultraviolet-ray blocking particles are coated onto and stably fixed into the surface of the infrared-ray blocking particle, it is possible to prevent aggregation of the ultraviolet-ray blocking particles, thereby preventing deterioration in uniformity of adhesion to the skin, and deterioration of the ultraviolet-ray blocking efficiency.

DESCRIPTION OF DRAWINGS

The patent or application file contains at least one drawing executed in color. Copies of this patent or patent application publication with color drawing(s) will be provided by the Office upon request and payment of the necessary fee.

BEST MODE

Figure 1:
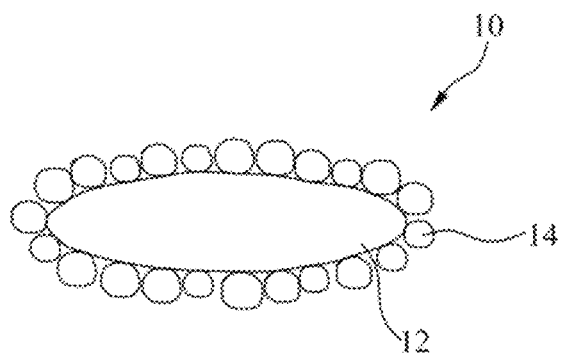
FIG. 1 is a cross section view illustrating composite powder according to one embodiment of the present invention.

If the human skin is exposed to solar rays, some of the solar rays is reflected or scattered on the stratum corneum, and the rest of the solar rays penetrates into the skin, whereby the skin damage may occur. Thus, in order to prepare powder for preventing the skin damage, it is first necessary to check what range of wavelength of the solar rays deeply penetrates into the inside of the skin. Thereafter, it needs to research and study a method for preparing the powder which enables to efficiently block the solar rays of the wavelength range which causes the skin damage.

The solar rays reaching the ground has the wavelength range of 290~4,000 nm, which may be divided into three ranges. That is, ultraviolet rays have the wavelength range of 290~400 nm, which occupy about 7% of the solar rays reaching the ground. Also, visible rays have the wavelength range of 400~760 nm, which occupy about 39% of the solar rays reaching the ground. Also, infrared rays have the wavelength of 760 nm ~1,000 μm, which occupy about 54% of the solar rays reaching the ground. The ultraviolet rays of the solar rays correspond to electromagnetic wave having the short wavelength range of 200~400 nm. In this case, since the ultraviolet rays having the wavelength range less than 290 nm are mostly lost while passing through the atmosphere, the virtual wavelength range of ultraviolet rays which causes the skin damage is about 290~400 nm. Especially, the ultraviolet rays within the wavelength range of 290~320 nm penetrates into the outermost layer of the skin, which might cause erythema, freckle, and edema. The ultraviolet rays within the wavelength range of 320~400 nm penetrate into the dermis, which induces melanin formation, and causes the skin cancer and wrinkles, thereby causing the skin aging and skin irritation.

The infrared rays of the solar rays correspond to nonionising electromagnetic wave having the long wavelength range of 760 nm ~1,000 μm, which may be generally divided into IRA (near IR, $\lambda$=760~1,440 nm), IRB (mid IR, $\lambda$=1, 440~3,000 nm), and IRC (far IR, $\lambda$=3,000 nm~1,000 μm).

The infrared rays are in the wavelength range with small photon energy. Thus, if the infrared rays are absorbed in the human body, it raises the temperature of the human body, but the infrared rays have been regarded as the rays having no adverse effects on the human body. However, the infrared rays of the relatively-short wavelength range, and more particularly, the infrared rays having the wavelength range of 760 nm~3,000 nm may induce the skin cancer, in the same manner as the ultraviolet rays.

Accordingly, the present invention is proposed based on a powder design which facilitates to efficiently block the ultraviolet rays having the wavelength range of 290 nm ~400 nm, and the infrared rays having the wavelength range of 760 nm~3,000 nm. That is, the composite powder of the present invention is prepared by the use of particles for blocking the ultraviolet rays, and particles for blocking the infrared rays. In more detail, the composite powder of the present invention is prepared by not only mixing the particles for blocking the ultraviolet rays with the particles for blocking the infrared rays, but also coating the particles for the infrared rays with the particles for the ultraviolet rays, to thereby maximize the efficiency in blocking the ultraviolet rays and infrared rays.

Reference will now be made in detail to the preferred embodiments of the present invention, examples of which are illustrated in the accompanying drawings.

FIG. 1 is a cross section view illustrating composite powder according to one embodiment of the present invention.

As shown in FIG. 1, the composite powder 10 according to one embodiment of the present invention is prepared by infrared-ray blocking particle 12, and a plurality of ultraviolet-ray blocking particles 14, wherein the surface of infrared-ray blocking particle 12 is coated with the plurality of ultraviolet-ray blocking particles 14.

As mentioned above, the infrared-ray blocking particle 12 is to efficiently block the infrared rays within the wavelength range of 760 nm ~3,000 nm and more preferably, the infrared rays within the wavelength range of 760 nm ~2,000 nm and most preferably, the infrared rays within the wavelength range of 760 nm~1,800 nm. However, the infrared-ray blocking particle 12 according to the present invention does not block only the infrared rays within the above wavelength range.

Preferably, a diameter of the infrared-ray blocking particle 12 is within the range of 0.38~1.5 µm. If the diameter of the infrared-ray blocking particle 12 is less than 0.38 µm, or more than 1.5 µm, it might deteriorate the efficiency in blocking the infrared rays within the wavelength range of 760 nm ~3,000 nm.

The infrared-ray blocking particle 12 may be formed of an inorganic-based material such as titanium dioxide ($TiO_2$) or zinc oxide (ZnO), but not necessary.

As mentioned above, the ultraviolet-ray blocking particles 14 are provided to efficiently block the ultraviolet rays within the wavelength range of 290 nm~400 nm, but it is not limited to the above wavelength range.

Preferably, a diameter of the ultraviolet-ray blocking particles 14 is within the range of 8~150 nm. If the diameter of the ultraviolet-ray blocking particles 14 is less than 8 nm, a coating process might be difficult due to strong aggregation. Meanwhile, if the diameter of the ultraviolet-ray blocking particles 14 is more than 150 nm, it might deteriorate the efficiency in blocking the ultraviolet rays within the above wavelength range.

The ultraviolet-ray blocking particles 14 may be formed of an inorganic-based material such as titanium dioxide ($TiO_2$), zinc oxide (ZnO), cerium dioxide ($CeO_2$), zirconium dioxide ($ZrO_2$), and etc., but it is not limited to these materials.

The entire surface of the infrared-ray blocking particle 12 may be coated with the ultraviolet-ray blocking particles 14, but not necessarily. Instead, the surface of the infrared-ray blocking particle 12 may be partially coated with the ultraviolet-ray blocking particles 14. For example, the ultraviolet-ray blocking particles 14 may be coated only onto the upper surface or lower surface of the infrared-ray blocking particle 12, instead of being coated onto the entire surfaces including the upper surface, lower surface, and lateral surfaces of the infrared-ray blocking particle 12. The ultraviolet-ray blocking efficiency can be realized even though the ultraviolet-ray blocking particles 14 are coated only onto the upper surface or lower surface of the infrared-ray blocking particle 12. Also, the ultraviolet-ray blocking efficiency can be realized even though the ultraviolet-ray blocking particles 14 are coated only onto predetermined portions of the upper surface of the infrared-ray blocking particle 12.

The ultraviolet-ray blocking particles 14 may be coated onto the surface of the infrared-ray blocking particle 12 while penetrating into the inside of the infrared-ray blocking particle 12. Herein, the shape of the ultraviolet-ray blocking particles 14 coated may be determined by a coating process. If applying a mechanical coating process which uses collision among the particles, the ultraviolet-ray blocking particles 14 may be coated while penetrating into the inside of the infrared-ray blocking particle 12 from the surface of the infrared-ray blocking particle 12.

The coating process for preparing the composite powder according to the present invention may use various coating methods which are generally known to those in the art, for example, mechanical coating method and method using the difference of isoelectric point. For example, on assumption that the method using the difference of isoelectric point is applied, since the isoelectric point of silica is about pH3, and the isoelectric point of $TiO_2$ is about pH6; silica is negative-charged, and $TiO_2$ is positive-charged, whereby silica-coated $TiO_2$ positively charged is formed by an electrostatic attraction between silica and $TiO_2$ when the pH difference is within the range of 3~6.

However, since the micro-sized titanium dioxide and the nano-sized titanium dioxide have the same isoelectric point, it is difficult to coat the nano-sized titanium dioxide onto the surface of the micro-sized titanium dioxide. Even though the nano-sized titanium dioxide is coated onto the surface of the micro-sized titanium dioxide, the nano-sized titanium dioxide is coated only small portions on the surface of the micro-sized titanium dioxide, whereby it is difficult to obtain the desired efficiency for blocking the ultraviolet rays. In order to solve these problems, the present invention uses the mechanical coating method to easily coat the nano-sized titanium dioxide onto the surface of the micro-sized titanium dioxide, especially, to improve the yield in coating without regard to the kind of the inorganic-based particle used.

Figure 10:
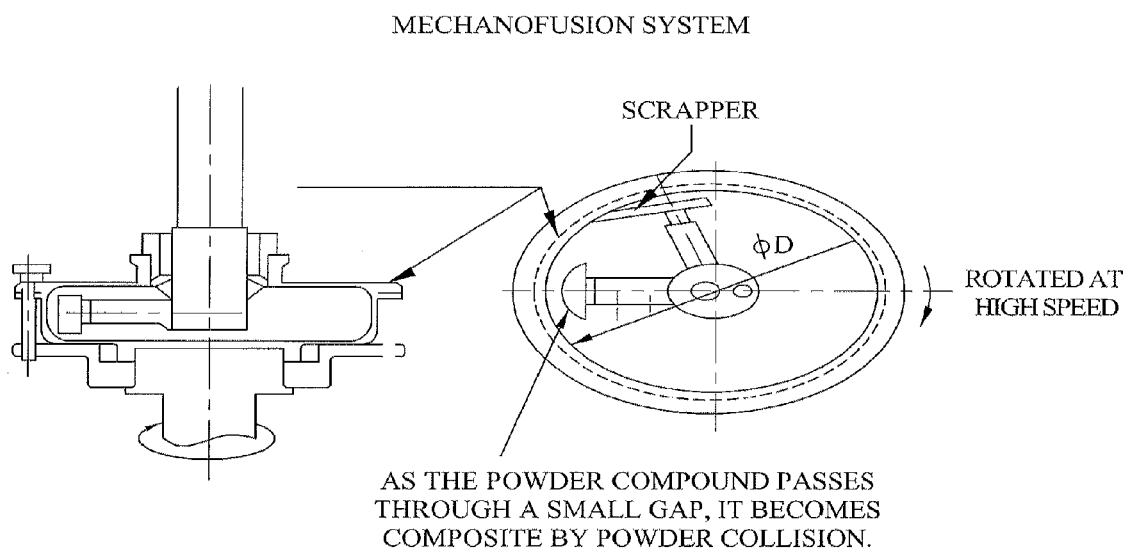
FIG. 10 shows an operational principle of Mechanofusion system of a mechanical method for preparing the composite powder of the present invention.
Figure 11:
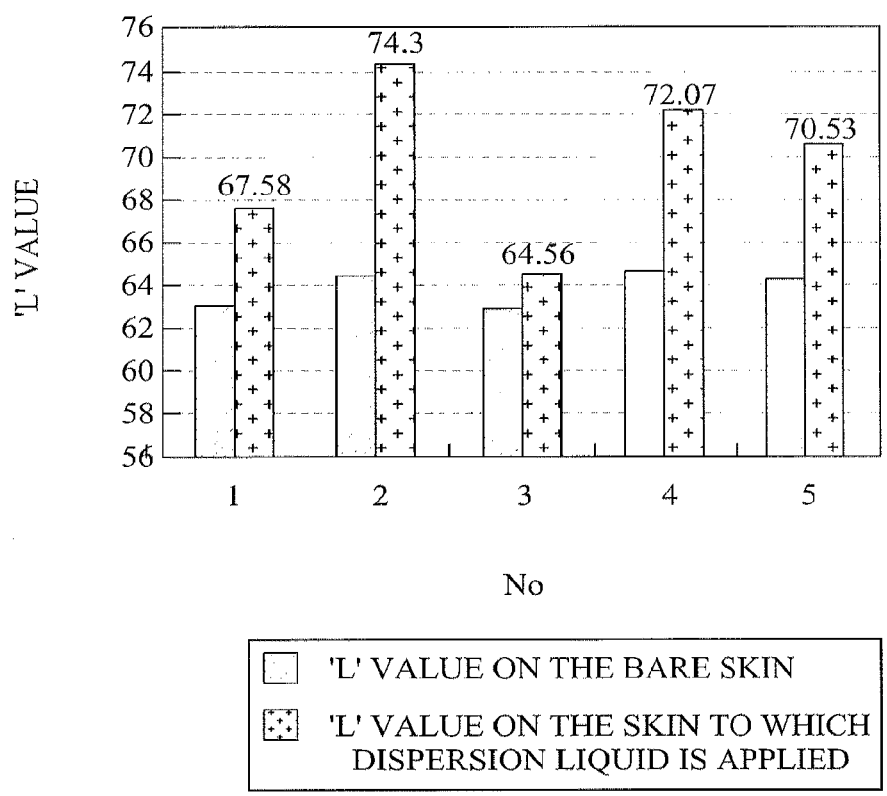
FIG. 11 is a 'L' value comparison graph to check a degree of white cloud in a dispersion liquid prepared by the composite powder of the present invention, wherein '1' is the example 8, '2' is the comparative example 7, '3' is the comparative example 8, '4' is the comparative example 9, and '5' is the comparative example 10.

Especially, the composite powder of the present invention may be prepared by a mechanical coating system of compression-shearing dry powder compounding method, that is, Mechanofusion system shown in FIG. 10. Mechanofusion system is provided with a rotating container being rotated at a high speed, and an arm head. As the powder compound passes through a small gap between the rotating container and the arm head, the compounding process is carried out by the particle collision.

However, the process for preparing the composite powder of the present invention is not limited to the case using the mechanical coating system. That is, the process for preparing the composite powder of the present invention may be performed by a wet compounding method using the isoelectric point, a high-speed impulsive method, or a dry compounding method using a mixing mode (compression, shearing).

Preferably, the ultraviolet-ray blocking particle and/or infrared-ray blocking particle constituting the composite powder of the present invention may be surface-treated with a surface treating agent. The surface treating agent may be formed of any material including one or more hydroxyl group (—OH) or hydrogen group (—H), for example, dimethiconol, triethoxycaprylylsilane, methicone/dimethicone copolymer, and methicone. Also, the surface treating agent may be formed of any inorganic material or organic material enabling to improve the surface quality of the powder, for example, alumina, silica, aluminum hydroxide, and etc., but it is not limited to these mentioned materials. If the composite powder is prepared after applying the surface treating agent to the surface of the ultraviolet-ray blocking particle and/or infrared-ray blocking particle, the ultraviolet-ray blocking particle is more uniformly coated onto the surface of the infrared-ray blocking particle.

In the composite powder 10 of the present invention, it is preferable that the infrared-ray blocking particles 12 be included to be not less than 1 weight %, and the ultraviolet-ray blocking particle 14 be included to be not less than 1 weight %, to thereby realize the good efficiency of blocking the ultraviolet rays and infrared rays at the same time. That is, a weight ratio of the infrared-ray blocking particle 12 to the ultraviolet-ray blocking particle 14 may be 1:99~99:1. Preferably, a weight ratio of the infrared-ray blocking particle 12 to the ultraviolet-ray blocking particle 14 may be 90:10~10:90, and more preferably, 80:20~20:80, and most preferably, 70:30.

The present invention may provide the cosmetics composition containing the above composite powder as an effective component. The infrared-ray blocking particle of the composite powder may be 1~25% by weight of the cosmetics composition, and more preferably 5~15% by weight of the cosmetics composition. If the infrared-ray blocking particle of the composite powder may be less than 1% by weight of the total weight of the cosmetics composition, it might be difficult to obtain the desired efficiency of blocking the ultraviolet rand infrared rays. Meanwhile, if the infrared-ray blocking particle of the composite powder may be more than 25% by weight of the total weight of the cosmetics composition, it might be restricted by a limited ingredient of cosmetics, and quality of prepared cosmetics, such as shapability, may be deteriorated due to the decrease in ratio of basic components for the cosmetics.

The cosmetic compound of the present invention may be prepared in any shape generally known to those in the art, for example, solution of water-in-oil emulsion or oil-in-water emulsion, suspension, emulsion, paste, gel, cream, lotion, powder, soap, surfactant-containing cleaning oil, powder-type foundation, emulsion-type foundation, wax-type foundation, or spray type.

The cosmetic compound of the present invention may be prepared in various shapes. In this case, the cosmetic compound of the present invention may contain auxiliary agent such as anti-oxidizing agent, stabilizing agent, dissolving agent, vitamin, pigment, and perfume; and/or carrier. The carrier to be used in accordance with the each type will be described as follows.

If the type corresponds to the powder or spray, the carrier may be made of lactose, talc, silica, aluminum hydroxide, calcium silicate, or polyamide powder. Especially, in case of the spray type, there may be used gas propellant such as chlorofluorohydrocarbon, propane/butane or dimethylether.

If the type corresponds to the solution or emulsion, the carrier may be made of solvent, dissolving agent, or emulsion agent, for example, water, ethanol, isopropanol, ethylcarbonate, ethylacetate, benzyl alcohol, benzyl benzoate, propyleneglycol, 1,3-butylglycol oil, glycerol aliphatic ester, polyethylene glycol, or sorbitan aliphatic ester.

If the type corresponds to the suspension, the carrier may be made of diluents such as water, ethanol or propyleneglycol; suspending agent such as ethoxylated isostearyl alcohol, polyoxyethylene sorbitol ester, or polyoxyethylene sorbitan ester; microcrystalline cellulose; aluminum metahydroxide; bentonite; aga; or tracanth.

If the type corresponds to the paste, cream or gel, the carrier may be made of animal oil, vegetable oil, wax, paraffin, tracanth, cellulose derivative, polyethyleneglycol, silicon, bentonite, silica, talc, or zinc oxide.

If the type corresponds to surfactant-containing cleaning, the carrier may be made of aliphatic alcohol sulfate, aliphatic alcohol ether sulfate, sulfosuccinic acid monoester, isethionate, imidazolinium derivative, methyl taurate, sarcosinate, aliphatic amide ether sulfate, alkyl amidobetains, aliphatic alcohol, aliphatic glyceride, aliphatic diethanolamide, vegetable oil, lanolin derivative, or ethoxyl glycerol aliphatic ester.

The composite powder of the present invention is prepared by using both the ultraviolet-ray blocking particle and the ultraviolet-ray blocking particle, thereby blocking both the ultraviolet rays and the infrared rays at the same time. Thus, if the composite powder of the present invention is applied to the cosmetics, it is possible to prevent the rough wrinkles, irregular pigmentary deposits, loss of skin elasticity, disturbance of skin barrier function, skin damages such as cancer of the skin, and skin aging, and also to boost SPF (Sun Protection Factor) and PA (Protection Factor of UVA) of the related art sunscreen by composition.

Especially, the present invention uses the composite powder prepared by coating one surface of the infrared-ray blocking particle with the ultraviolet-ray blocking particles, instead of mixing powder prepared by simply mixing the infrared-ray blocking particle and the ultraviolet-ray blocking particle. That is, since the small-sized ultraviolet-ray blocking particles are coated onto and stably fixed into the surface of the infrared-ray blocking particle, it is possible to prevent aggregation of the ultraviolet-ray blocking particles, thereby preventing deterioration in uniformity of adhesion to the skin, and deterioration of the ultraviolet-ray blocking efficiency.

Hereinafter, the detailed examples and experimental examples of the composite powder of the present invention will be described as follows.

EXAMPLES 1~5

Preparing the Composite Powder by Coating the Surface of the Infrared-Ray Blocking Particle with the Ultraviolet-Ray Blocking Particles A composite powder is prepared by using infrared-ray blocking powder MP-100 (produced by TAYCA Co.) having a particle size of 1 μm, and ultraviolet-ray blocking powder MPT-136 (produced by ISHIHARA SANGYO Co.) having a width of 8~20 nm and a length of 30~100 nm, wherein a weight ratio of infrared-ray blocking powder to ultraviolet-ray blocking powder may be changed as the following Table 1. The composite powder is prepared by the mechanical coating system of compression-shearing dry powder compounding method, that is, Mechanofusion system shown in FIG. 10.

Before preparing the composite powder, the aggregated ultraviolet-ray blocking powder MPT-136 is desorbed and crushed by the use of pin mill. In case of the examples 1~3, MP100 is used intactly, that is, MP-100 is coated with MPT-136. Meanwhile, in case of the examples 4 and 5, MP-100 whose surface is respectively treated with dimethiconol and dimethicone/methicone copolymer is coated with MPT-136. The mechanical coating system is performed at a rotation speed 8000 rpm by a coating process for 15 minutes. Also, in order to check enhancement of infrared-ray blocking efficiency and ultraviolet-ray blocking efficiency, the comparative examples 1 and 2 of the composite powder are prepared by using the infrared-ray blocking powder MP-100 (produced by TAYCA Co.) and the ultraviolet-ray blocking powder MPT-136 (produced by ISHIHARA SANGYO Co.), wherein the comparative examples 1 and 2 are prepared under the conditions of simple compounding method using Hensel mixer at 800 rpm for 5 minutes, and wherein the weight ratio of infrared-ray blocking powder to ultraviolet-ray blocking powder in the comparative example 1 is 70:30, and the weight ratio of infrared-ray blocking powder to ultraviolet-ray blocking powder in the comparative example 2 is 50:50.

The composite powder prepared by the above examples 1 to 5 and comparative examples 1 and 2 are summarized below in Table 1.

TABLE 1

| | Kind of Infrared-ray blocking powder/ Ultraviolet-ray blocking powder | Infrared-ray blocking powder weight % vs Ultraviolet-ray blocking powder weight % | Powder preparing method |
|---|---|---|---|
| Example 1 | MP-100/MPT-136 | 70:30 | Composite powder (coating) |
| Example 2 | MP-100/MPT-136 | 60:40 | Composite powder (coating) |
| Example 3 | MP-100/MPT-136 | 50:50 | Composite powder (coating) |
| Example 4 | MP-100 surface-treated with dimethiconol/ MPT-136 | 70:30 | Composite powder (coating after surface treatment) |
| Example 5 | MP-100 surface-treated with dimethicone and methicone copolymer/ MPT-136 | 70:30 | Composite powder (coating after surface treatment) |
| Comparative example 1 | MP-100/MPT-136 | 70:30 | Mixing powder (simple compounding) |
| Comparative example 2 | MP-100/MPT-136 | 50:50 | Mixing powder (simple compounding) |

EXAMPLE 6

Preparing Powder Cosmetics Composition Using Composite Powder

After the composite powder prepared by the example 1 is uniformly stirred by the use of Hensel mixer, liquid binder is uniformly sprayed by the use of micro-spray, and is then crushed by an atomizer, thereby preparing the powder foundation cosmetics composition (example 6). Also, powder foundation cosmetics composition (comparative example 3) is prepared by the use of composite powder of the comparative example 1 under the same method of the example 6. Also, powder foundation cosmetics composition (comparative example 4) is prepared by the use of only ultraviolet-ray blocking powder MPT-136 under the same method of the example 6. Also, powder foundation cosmetics composition (comparative example 5) is prepared by the use of only infrared-ray blocking powder MP-100 under the same method of the example 6.

The ingredients and weight % of the powder foundation cosmetics composition of the examples 6 and the comparative examples 3~5 are shown below in Table 2.

TABLE 2

| Ingredients of material | Example 6 (content %) | Comparative example 3 (content %) | Comparative example 4 (content %) | Comparative example 5 (content %) |
|---|---|---|---|---|
| Talc/cellulose/raffinose/PCA/dimethicone | 18.000 | 18.000 | 18.000 | 18.000 |
| Composite powder (example 1) | 20.000 | — | — | — |
| Mixing powder (comparative example 1) | — | 20.000 | — | — |
| Ultraviolet-ray blocking powder (MPT-136) | — | — | 20.000 | — |
| Infrared-ray blocking powder (MP-100) | — | — | — | 20.000 |
| Mica/hydrogenated lacithin | 15.000 | 15.000 | 15.000 | 15.000 |
| Mica/triethoxycaprylylsilane | 27.000 | 27.000 | 27.000 | 27.000 |
| Silica | 3.000 | 3.000 | 3.000 | 3.000 |
| Nylon-12 | 5.000 | 5.000 | 5.000 | 5.000 |
| Red iron oxide | 0.300 | 0.300 | 0.300 | 0.300 |
| Yellow iron oxide | 1.700 | 1.700 | 1.700 | 1.700 |
| Black iron oxide | 0.050 | 0.050 | 0.050 | 0.050 |
| Dimethicone | 1.950 | 1.950 | 1.950 | 1.950 |
| Phenyl trimethicone | 1.000 | 1.000 | 1.000 | 1.000 |
| Tricaprylin | 2.000 | 2.000 | 2.000 | 2.000 |
| Squalene0 | 5.000 | 5.000 | 5.000 | 5.000 |
| Total | 100.000 | 100.000 | 100.000 | 100.000 |

EXAMPLE 7

Preparing Water-in-Oil Emulsion Sunscreen Cosmetics Composition Using Composite Powder 15 weight % of the composite powder prepared by the example 1 is added into oil, and is then dispersed for 20 minutes by the use of homogenizer of 5,000 rpm, wherein the composition rate is shown below in Table 3. Thereafter, aqueous phase is slowly supplied to oily phase at 5,000 rpm of homogenizer, and is emulsified for 10 minutes, thereby preparing uniform sunscreen cosmetics of the example 7. Also, uniform sunscreen cosmetics (comparative example 6) which includes 15 weight % of the ultraviolet-ray blocking powder MPT-136 is obtained by the same method as that of the example 7.

Ingredients and contents of the water-in-oil emulsion sunscreen cosmetics composition according to the example 7 and the comparative example 6 are shown below in Table 3.

TABLE 3

| Ingredients of material | Example 7 | Comparative example 8 |
|---|---|---|
| Cyclomethicone | 6.60 | 6.60 |
| Neopenthylene | 7.50 | 7.50 |
| Polyglyceryl-6Polyricinoleate | 0.90 | 0.90 |
| Composite powder (example 1) | 15.00 | — |

TABLE 3-continued

| Ingredients of material | Example 7 | Comparative example 8 |
|---|---|---|
| Ultraviolet-ray blocking powder (MPT-136) | — | 15.00 |
| Dicaprylyl Carbonate | 5.00 | 5.00 |
| Dimethicone(6CS) | 3.00 | 3.00 |
| Cetyl PEG/PPG-10/1 Dimethicone | 2.00 | 2.00 |
| Quaternium-18 Hectorite | 0.80 | 0.80 |
| Refined water | 48.0 | 48.0 |
| Butylene glycol | 7.00 | 7.00 |
| Glycerin | 3.00 | 3.00 |
| Methylparaben | 0.20 | 0.20 |
| Sodium chloride | 1.00 | 1.00 |

EXAMPLE 8

Preparing Dispersion Using Composite Powder

The composite powder of the example 1 is dispersed at weight % shown in Table 4 for 20 minutes by the use of AGI MIXER of 300 RPM, thereby obtaining dispersion of the example 8. Under the same method as that of the example 8, dispersion of the comparative example 7 is obtained by the use of pigmentary titanium dioxide C47-056 (produced by SUN chemical Co.); dispersion of the comparative example 8 is obtained by the use of MPT-136; dispersion of the comparative example 9 is obtained by the use of MP-100; and dispersion of the comparative example 10 is obtained by the use of composite powder of the comparative example 1.

Ingredients and weight % of the dispersions of the example 8 and the comparative examples 7~10 are shown below in Table 4.

TABLE 4

| Ingredients of material | Example 8 | Comparative example 7 | Comparative example 8 | Comparative example 9 | Comparative example 10 |
|---|---|---|---|---|---|
| C12-15 Alkylbenzoate | 57.00 | 57.00 | 57.00 | 57.00 | 57.00 |
| Polyglyceryl-6Polyricinoleate | 3.00 | 3.00 | 3.00 | 3.00 | 3.00 |
| Composite powder (example 1) | 40.00 | — | — | — | — |
| pigmentary titanium dioxide C47-056 (produced by SUN chemical Co.) | — | 40.00 | — | — | — |
| Ultraviolet-ray blocking powder (MPT-136) | — | — | 40.00 | — | — |
| Infrared-ray blocking powder (MP-100) | — | — | — | 40.00 | — |
| Mixing powder (comparative example 1) | — | — | — | — | 40.00 |

EXPERIMENTAL EXAMPLE 1

Checking Formation of Composite Powder (SEM Photograph)

Figure 2:
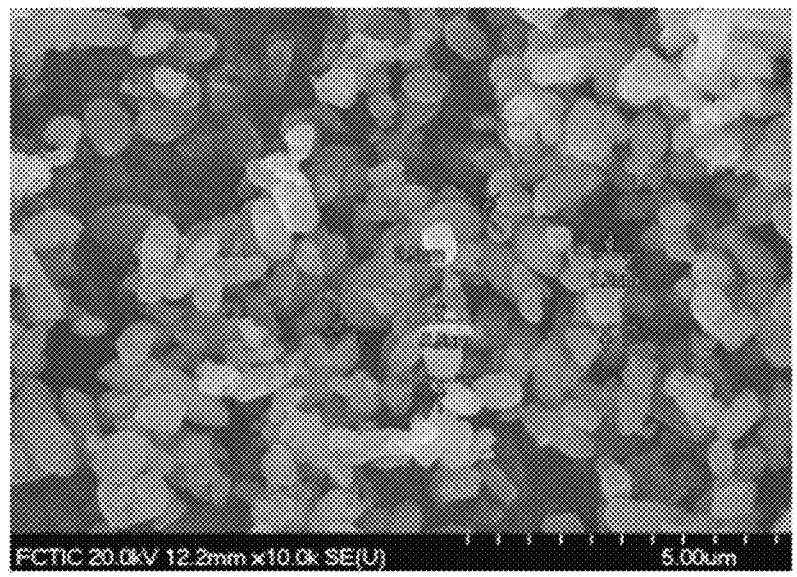
FIG. 2 is an SEM photograph of MP-100 showing infrared-ray blocking particle.
Figure 3:
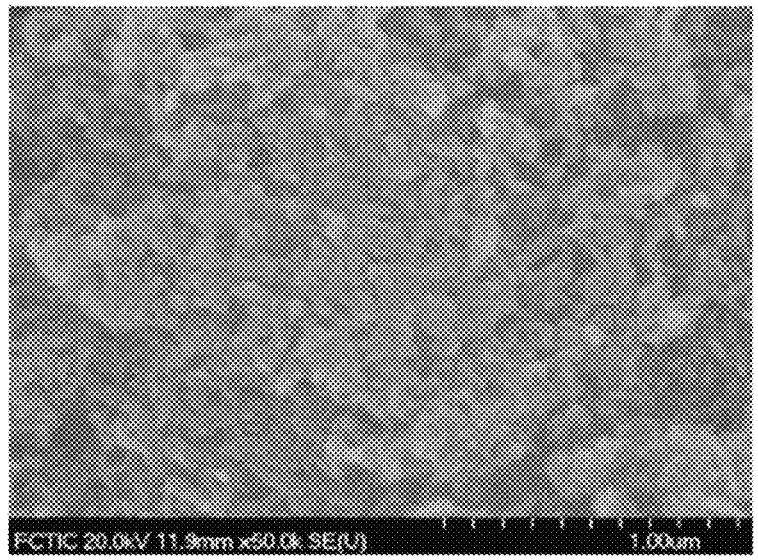
FIG. 3 is an SEM photograph of MPT-136 showing ultraviolet-ray blocking particle.

SEM photograph is taken to check whether or not the composite powder of the present invention obtained by coating the surface of the infrared-ray blocking particle with the ultraviolet-ray blocking particles is well made as desired. FIG. 2 is SEM photograph of infrared-ray blocking powder MP-100; and FIG. 3 is SEM photograph of ultraviolet-ray blocking powder MPT-136.

Figure 4:
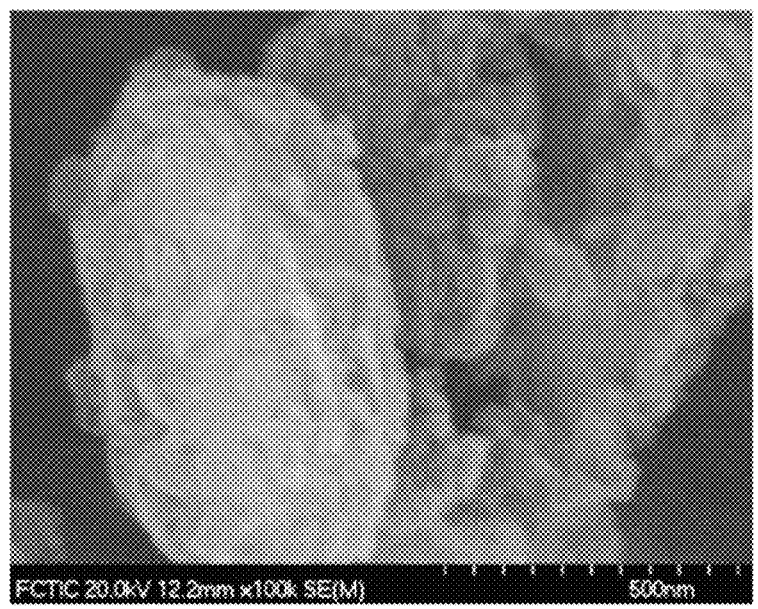
FIG. 4 is an SEM photograph showing composite powder according to the example 1 of the present invention.
Figure 5:
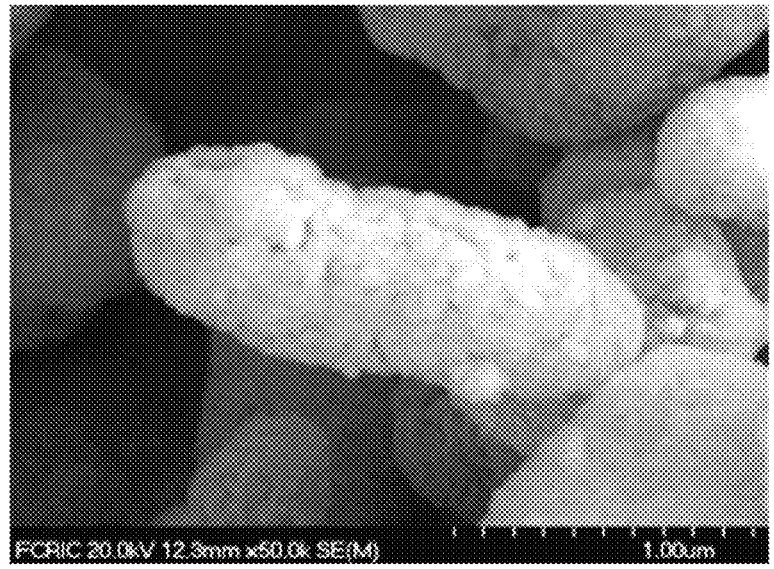
FIG. 5 is an SEM photograph showing composite powder according to the example 4 of the present invention.
Figure 6:
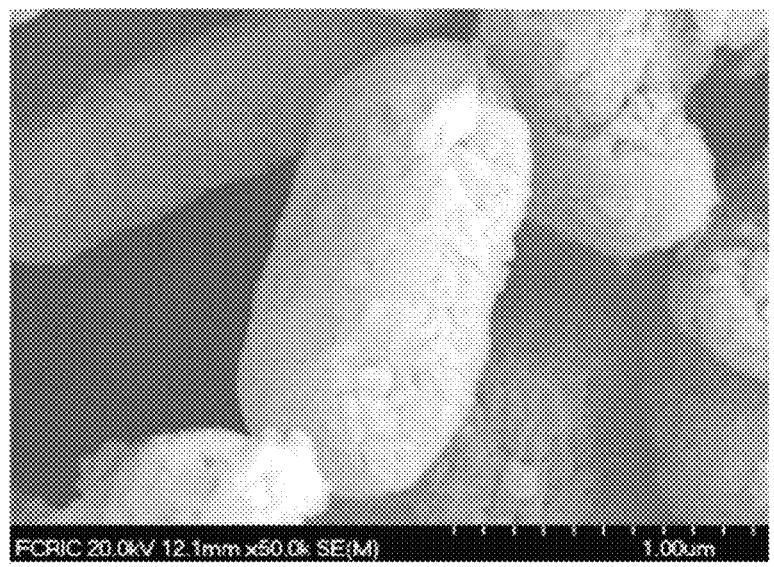
FIG. 6 is an SEM photograph showing composite powder according to the example 5 of the present invention.

FIG. 4 is SEM photograph of the composite powder prepared by the example 1; and FIGS. 5 and 6 are SEM photographs of the composite powder prepared by the examples 4 and 5.

As known from FIGS. 5 and 6, the surface of the surface-treated infrared-ray blocking particle is coated well with the ultraviolet-ray blocking particles. As known from FIG. 4, the surface of the surface-untreated infrared-ray blocking particle is also coated well with the ultraviolet-ray blocking particles. As a result, the composite powder prepared by coating the surface of the infrared-ray blocking particle with the ultraviolet-ray blocking particles may be made without regard to the surface treatment of the infrared-ray blocking particle.

Figure 7:
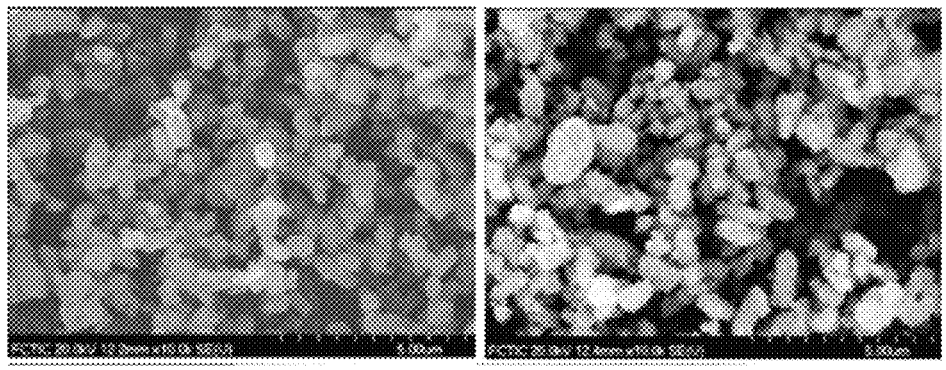
FIG. 7 shows SEM photographs of composite powder at the same scale before and after preparing processes to check whether or not the composite powder according to the example 1 is prepared properly; wherein the left photograph is an SEM photograph of MP-100 showing infrared-ray blocking particle, and the right photograph is an SEM photograph showing the composite powder of the example 1 prepared by coating the infrared-ray blocking particle MP-100 with the ultraviolet-ray blocking particle MPT-136.

FIG. 7 is SEM photograph which compares the SEM photograph (left photograph) of MP-100 with the SEM photograph (right photograph) of the composite powder of the example 1 prepared by coating the surface of MP-100 with MPT-136 at the same magnification. As known from FIG. 7, the composite powder of the present invention is made definitely.

EXPERIMENTAL EXAMPLE 2

Coating Strength Test of Composite Powder

Figure 8:
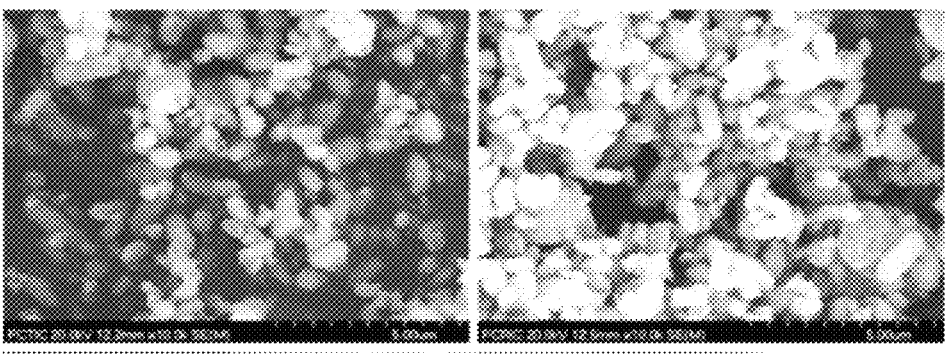
FIG. 8 shows SEM photographs of composite powder before and after crushing process to check a coating strength of the composite powder of the example 1 by applying a physical force to the composite powder, wherein the left photograph is an SEM photograph before the crushing process, and the right photograph is an SEM photograph after the crushing process.
Figure 9:
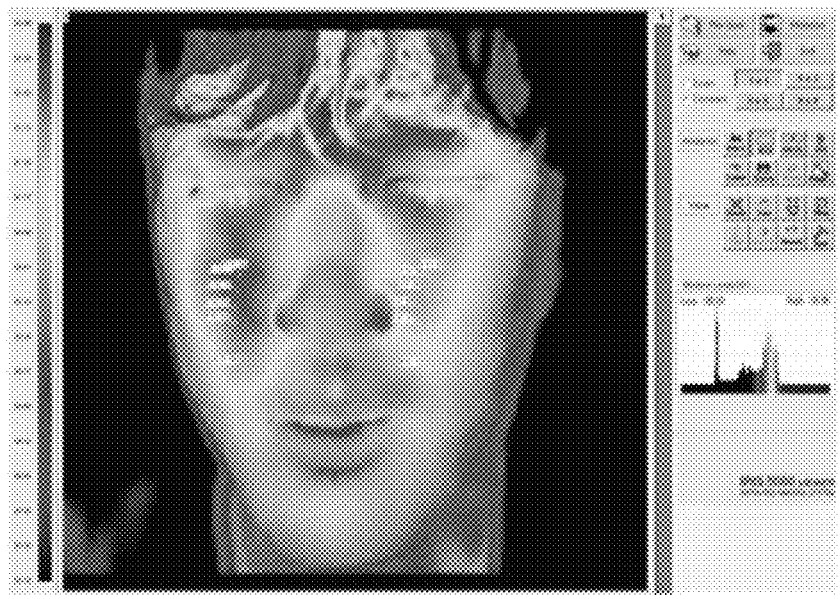
FIG. 9 shows a photograph taken by a thermal imaging camera, which shows that sunscreen cosmetic (example 7) containing the composite powder of the present invention is effective in blocking rays, wherein the left photograph shows cosmetics of the comparative example 7 (containing MPT-136), and the right photograph shows cosmetics of the example 7 (composite powder of the example 1).

In order to check a coating strength of the composite powder prepared by the example 1, the composite powder is crushed for 30 seconds (two times, 15 seconds each) by the use of IKA Mixer (Model name: IKA-WERKE M20), and then the surface state thereof is observed by SEM. The result is shown in FIG. 8. As shown in FIG. 8, the surface after the crushing process (right photograph) is hardly changed from the surface before the crushing process (left photograph). Thus, the coating state of the ultraviolet-ray blocking powder before the crushing process is maintained intactly even after the crushing process. In order to check the coating state of the composite powder prepared by the example 1, ultraviolet-ray blocking efficiency of the composite powder after the crushing process is compared with ultraviolet-ray blocking efficiency of the composite powder before the crushing process by the use of SPF 290 analyzer (Optometrics USA, Inc) of In-vitro test method. In more detail, butylenes glycol and the composite powder before the crushing process or after the crushing process are mixed at a ratio of 1:1, and are then dispersed uniformly; and appropriate amount (2 mg/cm$^2$) of the dispersed mixture is uniformly pasted on a surgical tape (Transpore tape produced by 3M Co.), and is dried for 15~20 minutes. Then, the ultraviolet-ray blocking efficiency of SPF (sun protection factor) and PA (protection factor of UVA) is measured. In each sample, the above SPF and PA are measured five times, and the mean value is shown as SPF value and PA value, which is shown below in Table 5. As known from below Table 5, the SPF value and PA value after the crushing process are very similar to those before the crushing process. As a result, it is known that the coating state of the composite powder after the crushing process is very similar to that of the composite powder before the crushing process.

TABLE 5

| Example 1 | SPF value | PA value |
|---|---|---|
| Before crushing | 19.23 | 22.34 |
| After crushing | 18.58 | 20.77 |

EXPERIMENTAL EXAMPLE 3

Test of Ultraviolet-Ray Blocking Efficiency (SPF Value and PA Value) of Composite Powder Ultraviolet-ray blocking efficiencies in the powder of infrared-ray blocking powder MP-100, the powder of ultraviolet-ray blocking powder MPT-136, the composite powder of the example 1, the composite powder of the example 3, the mixing powder of the comparative example 1, and the mixing powder of the comparative example 2 are compared by the use of SPF 290 analyzer (Optometrics USA, Inc) of In-vitro test method. In more detail, butylenes glycol is mixed with each of the powder MP-100, the powder MPT-136, the composite powder, and the mixing powder, wherein a mixing ratio of butylenes glycol to each powder is 1:1; and is then dispersed uniformly. Thereafter, the appropriate amount (2 mg/cm$^2$) of the dispersed mixture is uniformly pasted on a surgical tape (Transpore tape produced by 3M Co.), and is dried for 15~20 minutes. Then, the ultraviolet-ray blocking efficiency of SPF (sun protection factor) and PA (protection factor of UVA) is measured. In each sample, the above SPF and PA are measured five times, and the mean value is used to obtain SPF value and PA value which are shown below in Table 6.

As known from below Table 6, the SPF value and PA value in the comparative example 1, comparative example 2, example 1, and example 3 are higher than the SPF value and PA value in MP-100 powder and MPT-136 powder. Thus, it is known that the simple mixing of the ultraviolet-ray blocking powder and the infrared-ray blocking powder enhances the ultraviolet-ray blocking efficiency.

In comparison to the SP value and PA value in the mixing powder of the comparative example 1, the SPF value in the composite powder of the example 1 is raised by about 18%, and the PA value in the composite powder of the example 1 is raised by about 20%. In comparison to the SP value and PA value in the mixing powder of the comparative example 2, the SPF value in the composite powder of the example 3 is raised by about 20%, and the PA value in the composite powder of the example 3 is raised by about 32%. Thus, it is known that the ultraviolet-ray blocking efficiency of the composite powder is relatively higher than the ultraviolet-ray blocking efficiency of the mixing powder prepared by the simple mixing.

Also, the SPF value and PA value in the mixing powder of the comparative example 1 are higher than the SP value and PA value in the mixing powder of the comparative example 2; and the SPF value and PA value in the composite powder of the example 1 are higher than the SP value and PA value in the composite powder of the example 3. Thus, it is known that the SPF value and PA value are enhanced when a weight ratio of the infrared-ray blocking powder to the ultraviolet-ray blocking powder is 70:30.

TABLE 6

| | SPF value | PA value |
|---|---|---|
| MP-100 | 7.47 | 7.92 |
| MPT-136 | 11.15 | 9.7 |
| Comparative example 1 (mixing powder) | 17.74 | 20.90 |
| Example 1 (composite powder) | 20.87 | 25.10 |
| Comparative example 2 (mixing powder) | 15.75 | 15.82 |
| Example 3 (composite powder) | 18.97 | 20.91 |

EXPERIMENTAL EXAMPLE 4

Test of Ultraviolet-Ray Blocking Efficiency of Cosmetics Composition

The ultraviolet-ray blocking efficiency in the powder foundation cosmetics composition prepared by the example 6, and the cosmetics composition prepared by the comparative example 3 is measured in the same method as that of the experimental example 3, whereby the results are shown below in Table 7. As known from below Table 7, in comparison to the comparative example 3, the SPF value of the example 6 is raised by about 32%, and the PA value of the example 6 is raised by about 36%. Thus, it is known that enhancement of the ultraviolet-ray blocking efficiency of the SPF value and PA value in the composite powder affects enhancement of the ultraviolet-ray blocking efficiency of the SPF value and PA value in the cosmetics composition.

TABLE 7

| | SPF value | PA value |
|---|---|---|
| Comparative example 3 (cosmetics using mixing powder) | 13.10 | 13.41 |
| Example 8 (cosmetics using composite powder) | 17.23 | 18.21 |

EXPERIMENTAL EXAMPLE 5

Functional Evaluation of the Powder Foundation of Example 6 and Comparative Examples 3~5

The functional evaluation is performed by applying the foundation powder, which is prepared by the example 6 and comparative examples 3~5, onto the skin of 20 women. This functional evaluation is to check whether or not the powder foundation satisfies following matters: even cosmetic film, cosmetic film being blended into skin, moderate glossy feeling, satisfactory spreadability, good adhesion, difference between apparent color and tine of cosmetic film, and soft focus effect. The results are shown below in Table 8.

TABLE 8

Test results of functional evaluation

| Test samples | | Cosmetic film | | | | | Difference between apparent color and tone of cosmetic film | Soft focus effect |
|---|---|---|---|---|---|---|---|---|
| Number of example | Number of comparative example | Even cosmetic film | being blended into skin | Moderate glossy feeling | satisfactory spreadability | Good adhesion | | |
| 6 | | ⊙ | ○ | ○ | ⊙ | ⊙ | ○ | ⊙ |
| | 3 | Δ | ○ | ○ | ○ | Δ | ○ | ○ |
| | 4 | Δ | ⊙ | Δ | X | Δ | ⊙ | Δ |
| | 5 | ○ | Δ | ○ | ○ | ○ | Δ | Δ |

⊙: optimal use feeling or touch feeling
○: moderate use feeling or touch feeling
Δ: somewhat unsatisfactory
X: obvious unsatisfactory As known from above Table 8, the powder foundation (example 6) prepared by compounding the composite powder of the present invention has the great properties such as the even cosmetic film, satisfactory spreadability, good adhesion, and soft focus effect. Also, the composite powder of the present invention is superior in all evaluation items to the mixing powder of the comparative example 3.

In addition, the composite powder including the ultraviolet-ray blocking particle and infrared-ray blocking particle according to the present invention can obtain the even cosmetic film, satisfactory spreadability, good adhesion, and soft focus effect, which are not obtainable in the mixing powder. It is known that the above properties of the even cosmetic film, satisfactory spreadability, good adhesion, and soft focus effect are derived from the uniform dispersion effect of the ultraviolet-ray blocking particle MPT-136, that is, even cosmetic film.

EXPERIMENTAL EXAMPLE 6

Test of Infrared-Ray Blocking Efficiency of Cosmetics Composition

In order to measure the infrared-ray blocking efficiency of the cosmetics composition containing the composite powder of the present invention, the following tests are carried out.

After applying the appropriate amount (2 mg/cm$^2$) of the respective cosmetics compositions prepared by the example 6, and comparative examples 4~5 to the skin of the humeral region of the arm, it is irradiated at a distance of 60 cm for 10 minutes by the use of infrared lamp (125 W), and then a temperature of the skin is measured in a non-contact method by the use of Laser Radiation Gun Thermometer. The results are shown below in Table 9.

As known from Table 9, when the infrared ray is applied to the skin, the temperature rise in the skin to which the cosmetics composition (comparative example 5) prepared by the infrared-ray blocking powder, and the skin to which the cosmetics composition (example 6) prepared by the composite powder of the present invention is relatively smaller than the temperature rise in the untreated skin, and the skin to which the cosmetics composition (comparative example 4) prepared by the ultraviolet-ray blocking powder. Thus, it is known that the cosmetics composition prepared by the example 6 and the comparative example 5 has the infrared-ray blocking efficiency.

Also, the infrared-ray blocking efficiency in the cosmetics composition (comparative example 5) prepared by the infrared-ray blocking powder is very similar to the infrared-ray blocking efficiency in the cosmetics composition (example 6) prepared by the composite powder of the present invention. This means that the infrared-ray blocking efficiency is maintained even though the infrared-ray blocking powder is coated with the ultraviolet-ray blocking powder. Thus, it shows that the composite powder of the present invention has the infrared-ray blocking efficiency.

TABLE 9

| | Before applying (° C.) | 10 minutes later, after applying (° C.) |
|---|---|---|
| Untreated skin | 30.1 | 36.1 |
| Comparative example 4 | 29.9 | 35.35 |
| Comparative example 5 | 30.3 | 34.68 |
| Example 6 | 30.3 | 34.37 |

After uniformly applying the appropriate amount (2 mg/cm$^2$) of the respective cosmetics compositions prepared by the example 7, and comparative example 6 to a half of the face, it is irradiated at a distance of 60 cm for 10 minutes by the use of infrared lamp (125 W), and then a temperature of the skin on the cheek is measured by the use of Thermography (IRIS-5000) corresponding to a skin-temperature tester using infrared thermography. The measured results are shown above in Table 9.

As known from Table 9, on comparison of the composition (comparative example 6) prepared by the ultraviolet-ray blocking powder to the cosmetics composition (example 7) prepared by the composite powder of the present invention, the example 7 prepared by the composite powder shows that there are a small-sized red portion and a large-sized blue portion on the cheek. If it is calculated in terms of temperature, it shows that the average temperature is lowered by about 0.5° C. That is, it is known that the infrared rays which cause the temperature rise are blocked effectively.

EXPERIMENTAL EXAMPLE 7

Test of Degree of White Cloud in the Dispersion of the Composite Powder

In order to measure whiteness of the dispersion containing the composite powder of the present invention, the following test is carried out. The dispersions prepared by the example 8 and the comparative examples 7~10 are used to measure a degree of white cloud. In each square-shaped portion (2×2 cm²) of 6 squares on the bare skin of the upper arm, 'L' value is measured by the use of colorimeter (Minolta CR-200). Also, correctly-weighted 0.1 g of each of samples prepared by the example 8 and the comparative examples 7~10 is applied to the bare skin, and is rubbed with finger thirty times, and then 'L' value is measured by the use of colorimeter, after 5 minutes. The difference between the 'L' value measured on the bare skin and the 'L' value measured after applying each sample is evaluated. As the difference of 'L' value becomes larger, the degree of white cloud becomes larger. Meanwhile, as the difference of 'L' value becomes smaller, the degree of white cloud becomes smaller.

As a result, the difference of 'L' value in the example 8 is 4.5; the difference of 'L' value in the comparative example 7 is 9.85; the difference of 'L' value in the comparative example 8 is 1.63; the difference of 'L' value in the comparative example 9 is 7.41; and the difference of 'L' value in the comparative example 10 is 6.30.

Thus, the degree of white cloud in the composite powder of the example 8 is higher than the degree of white cloud in the ultraviolet-ray blocking powder of the comparative example 8, wherein it is known that the ultraviolet-ray blocking powder is transparent while being applied to the skin. However, the degree of white cloud in the composite powder of the example 8 is lower than the degree of white cloud in the pigmentary titanium dioxide of the comparative example 7 and the mixing powder of the comparative example 10. Accordingly, the composite powder may be used for various products, for example, powder type, sunscreen type, whitening emulsion type, and etc.

EXPERIMENTAL EXAMPLE 8

Skin Irritation Test

For 20 test applicants, a skin patch test is carried out by uniformly dispersing each sample of the composite powder of the examples 1~3, the mixing powder of the comparative examples 1~2, the cosmetics of the example 6, and the cosmetics of the comparative example 3 in a solvent of squalene without causing skin irritation, to thereby test skin irritation. The results are shown below in Table 10. In general, as shown in Table 10, there are no skin troubles. In case of the examples 2 and 6 and the comparative example 3, there is one person having slight skin troubles. However, one person among the test applicants shows the allergic skin reaction by a skin analyzing test. Thus, it is safe to apply the composite powder of the present invention to the skin.

What is claimed is:
1. A composite powder comprising:
    infrared-ray blocking particles; and
    ultraviolet-ray blocking particles coated onto one surface of each of the infrared-ray blocking particles
    wherein the ultraviolet-ray blocking particles are coated onto the surface of the infrared-ray blocking particle while penetrating into the inside of the infrared-ray blocking particle, and
    wherein a diameter of the infrared-ray blocking particle is within the range of 0.38-1.5 μm; and a diameter of the ultraviolet-ray blocking particle is within the range of 8-150 nm.
2. The composite powder of claim 1, wherein the ultraviolet-ray blocking particles are coated onto the entire surface of the infrared-ray blocking particle.
3. The composite powder of claim 1, wherein at least one of the infrared-ray blocking particle and ultraviolet-ray blocking particle is surface-treated with an organic or inorganic surface treating agent containing a hydroxyl group (—OH) or hydrogen group (—H).
4. The composite powder of claim 1, wherein a weight ratio of the ultraviolet-ray blocking particle to the infrared-ray blocking particle is 1:99-99:1.
5. The composite powder of claim 1, wherein a weight ratio of the infrared-ray blocking particle to the ultraviolet-ray blocking particle is 90:10-10:90.
6. The composite powder of claim 1, wherein a weight ratio of the ultraviolet-ray blocking particle to the infrared-ray blocking particle is 70:30.
7. The composite powder of claim 1, wherein the infrared-ray blocking particle is formed of titanium dioxide ($TiO_2$) or zinc oxide (ZnO), and the ultraviolet-ray blocking particle is formed of a material or a mixture of materials selected from a group including titanium dioxide ($TiO_2$), zinc oxide (ZnO), cerium dioxide ($CeO_2$), and zirconium dioxide ($ZrO_2$).
8. The composite powder of claim 1, wherein the infrared-ray blocking particle blocks infrared rays having the wavelength range of 760 nm-3000 nm; and the ultraviolet-ray blocking particle blocks ultraviolet rays having the wavelength range of 290 nm-400 nm.
9. A cosmetics composition comprising the composite powder of claim 1 as an effective component.
10. The cosmetics composition of claim 9, wherein the infrared-ray blocking particle of the composite powder is about 1%-25% by weight of the cosmetics composition.
11. The cosmetics composition of claim 9, wherein the infrared-ray blocking particle of the composite powder is about 5%-15% by weight of the cosmetics composition.

TABLE 10

|  | Example 1 Composite powder | Example 2 Composite powder | Example 3 Composite powder | Example 6 Cosmetics composition | Comparative example 1 Mixing powder | Comparative example 2 mixing powder | Comparative example 3 cosmetics |
|---|---|---|---|---|---|---|---|
| +++ | 0 | 0 | 0 | 0 | 0 | 0 | 0 |
| ++ | 0 | 0 | 0 | 0 | 0 | 0 | 0 |
| + | 0 | 1 | 0 | 1 | 0 | 0 | 1 |
| ± | 15 | 12 | 16 | 14 | 17 | 18 | 15 |
| − | 5 | 7 | 4 | 5 | 3 | 2 | 4 |

Evaluation standard:
+++ (strong trouble),
++ (weak trouble),
+ (very weak trouble)
± (normal),
− (negative)

12. The cosmetics composition of claim 9, wherein the cosmetics composition is prepared in type of a solution of water-in-oil emulsion or oil-in-water emulsion, suspension, emulsion, paste, gel, cream, lotion, powder, soap, surfactant-containing cleaning oil, powder-type foundation, emulsion-type foundation, wax-type foundation, or spray type.

\* \* \* \* \*